US008871485B2

(12) United States Patent
McKenna et al.

(10) Patent No.: US 8,871,485 B2
(45) Date of Patent: Oct. 28, 2014

(54) MODIFIED CARBONIC ANHYDRASE ENZYMES AND THEIR USE IN CARBON DIOXIDE SEQUESTRATION AND ELIMINATION

(75) Inventors: Robert McKenna, Gainesville, FL (US); David N. Silverman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/805,752

(22) PCT Filed: Jun. 22, 2011

(86) PCT No.: PCT/US2011/041385
§ 371 (c)(1),
(2), (4) Date: Mar. 7, 2013

(87) PCT Pub. No.: WO2011/163323
PCT Pub. Date: Dec. 29, 2011

(65) Prior Publication Data
US 2013/0171720 A1      Jul. 4, 2013

Related U.S. Application Data

(60) Provisional application No. 61/357,626, filed on Jun. 23, 2010.

(51) Int. Cl.
| | |
|---|---|
| *C12N 9/16* | (2006.01) |
| *C12N 9/88* | (2006.01) |
| *C02F 3/34* | (2006.01) |
| *A61L 9/01* | (2006.01) |
| *C07H 21/04* | (2006.01) |
| *B01D 53/00* | (2006.01) |
| *C12Q 1/527* | (2006.01) |
| *B01D 53/62* | (2006.01) |
| *C12P 3/00* | (2006.01) |
| *B01D 53/14* | (2006.01) |

(52) U.S. Cl.
CPC ............... *B01D 53/00* (2013.01); *Y02C 10/04* (2013.01); *B01D 2251/404* (2013.01); *C12Q 1/527* (2013.01); *B01D 2255/804* (2013.01); *B01D 2252/103* (2013.01); *B01D 53/62* (2013.01); *C12P 3/00* (2013.01); *B01D 2251/402* (2013.01); *B01D 53/1493* (2013.01); *C12N 9/88* (2013.01)
USPC ........... 435/196; 435/232; 435/262; 435/266; 536/23.2

(58) Field of Classification Search
None
See application file for complete search history.

(56) References Cited

U.S. PATENT DOCUMENTS

| | | | |
|---|---|---|---|
| 3,659,400 A | 5/1972 | Kester | |
| 3,853,712 A | 12/1974 | House et al. | |
| 4,032,616 A | 6/1977 | Artur et al. | |
| 4,047,894 A | 9/1977 | Kuhl | |
| 4,162,298 A | 7/1979 | Holladay et al. | |
| 4,452,676 A | 6/1984 | Birbara et al. | |
| 4,521,387 A | 6/1985 | Broecker et al. | |
| 4,710,362 A | 12/1987 | Nieh | |
| 5,061,455 A | 10/1991 | Brose et al. | |
| 5,112,740 A | 5/1992 | Nealon et al. | |
| 5,565,319 A | 10/1996 | Pedersen et al. | |
| 5,609,838 A | 3/1997 | Neuman et al. | |
| 5,618,506 A | 4/1997 | Suzuki et al. | |
| 5,624,812 A | 4/1997 | Hattori et al. | |
| 5,674,463 A | 10/1997 | Dao et al. | |
| 5,690,099 A | 11/1997 | Abramov et al. | |
| 7,083,730 B2 | 8/2006 | Davis | |
| 7,132,090 B2 | 11/2006 | Dziedzic et al. | |
| 7,459,088 B2 | 12/2008 | Davis | |
| 2005/0145568 A1 | 7/2005 | McGinnis | |
| 2006/0257990 A1 | 11/2006 | Daigle et al. | |
| 2009/0297431 A1 | 12/2009 | McGinnis et al. | |
| 2010/0108587 A1 | 5/2010 | McGinnis | |

FOREIGN PATENT DOCUMENTS

WO     96/40414     12/1996

OTHER PUBLICATIONS

Fisher et al. Speeding up proton transfer in a fast enzyme: kinetic and crystallographic studies on the effect of hydrophobic amino acid substitutions in an active site of human carbonic anhydrase II, Biochemistry (2007), 46: 3803-3813.*
Genis et al. Design of a Carbonic Anhydrase IX Active-Site Mimic to Screen Inhibitors for Possible Anticancer Properties, Biochemistry 2009, 48, 1322-1331, Epub Jan. 26, 2009.*
Liang, Z et al., "Importance of the conserved active-site residues Tyr7, Glu106 and Thr199 for the catalytic function of human carbonic anhydrase II", Eur. J. Biochem, 1993, vol. 211, pp. 821-827.
Mirjafari, P. et al., "Investigating the Application of Enzyme Carbonic Anhydrase for C02 Sequestration Purposes", Ind. Eng. Chem. Res, 2007, vol. 46, pp. 921-926.
Carter et al., "Improved oligonucleotide site-directed mutagenesis using M13 vectors", Nucl. Acids Res., vol. 13, pp. 4431-4443 (1985).

(Continued)

*Primary Examiner* — Iqbal H Chowdhury
(74) *Attorney, Agent, or Firm* — Timothy H. Van Dyke; Beusse, Wolter, Sanks & Maire, P.A.

(57) ABSTRACT

Disclosed herein are modified carbonic anhydrase enzymes, and a process of using same for the extraction, production and purification of carbon dioxide gas. More particularly, modified carbonic anhydrase enzymes are used for the production, purification of carbon dioxide and the products of the hydration reaction, hydrogen and bicarbonate ions Also, this technology is used to enhance the production of carbon dioxide in blood or in reverse osmosis desalination to remove carbon dioxide. Specifically, the invention relates to a modified carbonic anhydrase enzyme possessing improved activity and a process whereby immobilized modified carbonic anhydrase contained within a reactor device catalyzes the reversible hydration of carbon dioxide.

16 Claims, 2 Drawing Sheets

(56) References Cited

OTHER PUBLICATIONS

Wells et al., "Importance of hydrogen-bond formation in stabilizing the transition state of subtilisin", Phil. Trans. R. Soc. Lond.; vol. 317: pp. 415-423 (1986); Abstract Only.
Eghtedarzadeh, et al, "Use of oligonucleotides to generate large deletions, Nucl." Acids Res. vol. 14: pp. 5115 (1986); Abstract Only.
Carter, "Site-directed mutagenesis", Biochem. J.; vol. 237: pp. 1-7 (1986).
W. P. C. Stemmer, "Rapid Evolution of a Protein in Vitro by DNA Shuffling", Nature, vol. 370, pp. 389-391 (1994); abstract only.
Kunkel, "Rapid and efficient site-specific mutagenesis without phenotypic selection", Proc. Natl. Acad. Sci. USA; vol. 82: pp. 488-492 (1985).
I. A. Lorimer, et al, "Random recombination of antibody single chain Fv sequences after fragmentation with DNaseI in the presence of Mn2+", Nucleic Acids Res., vol. 23, pp. 3067-3068 (1995).
Sakmar, et al, "Total synthesis and expression of a gene for the a-subunit of bovine rod outer segment guanine nucleotide-binding protein (transducin)", Nucl. Acids Res.; vol. 14: pp. 6361-6372 (1988).
Wells et al., "Cassette mutagenesis: an efficient method for generation of multiple mutations at defined sites", Gene; vol. 34:315-323 (1985); abstract only.
Grundstrom et al., "Oligonucleotide-directed mutagenesis by microscale 'shot-gun' gene synthesis", Nucl. Acids Res.; vol. 13: pp. 3305-3316 (1985).
Zoller, et al, "Oligonucleotide-directed mutagenesis: a simple method using two oligonucleotide primers and a single-stranded DNA template", Methods in Enzymol.; vol. 154: pp. 329-350 (1987).
Taylor et al., "The use of phosphorothioate-modified DNA in restriction enzyme reactions to prepare nicked DNA", Nucl. Acids Res.; vol. 13: pp. 8749-8764 (1985).
Taylor et al., "The rapid generation of oligonucleotide-directed mutations at high frequency using phosphorothioate-modified DNA", Nucl. Acids Res.; vol. 13: pp. 8765-8785 (1985).
Nakamaye, et al, "Inhibition of restriction endonuclease Nci I cleavage by phosphorothioate groups and its application to oligonucleotide-directed mutagenesis", Nucl. Acids Res. vol. 14: pp. 9679-9698 (1986).
Sayers et al., "5'-3' Exonucleases in phosphorothioate-based oligonucleotide-directed mutagenesis", Nucl. Acids Res. vol. 16: pp. 791-802 (1988).
Mandecki, "Oligonucleotide-directed double-strand break repair in plasmids of *Escherichia coli*: a method for site-specific mutagenesis", Proc. Natl. Acad. Sci. USA, vol. 83: pp. 7177-7181 (1986).
Kramer et al., "The gapped duplex DNA approach to oligonucleotide-directed mutation construction", Nucl. Acids Res. vol. 12: pp. 9441-9456 (1984).
Arnold, "Protein engineering for unusual environments", Current Opinion in Biotechnology, vol. 4,pp. 450-455 (1993); abstract only.
Kramer et al., "Improved enzymatic in vitro reactions in the gapped duplex DNA approach to oligonucleotide-directed construction of mutations", Nucl. Acids Res. vol. 16: pp. 7207 (1988); abstract only.
Fritz et al., "Oligonucleotide-directed construction of mutations: a gapped duplex DNA procedure without enzymatic reactions in vitro", Nucl. Acids Res. vol. 16: pp. 6987-6999 (1988).
Sieber, et al., "Libraries of Hybrid Proteins From Distantly Related Sequences", Nature Biotechnology, vol. 19: pp. 456-460 (2001); abstract only.
Botstein et al., "Strategies and applications of in vitro mutagenesis", Science, 1985, vol. 229, pp. 1193-1201.
Zheng, J. et al., "Role of Hydrophilic Residues in Proton Transfer During Catalysis by Human Carbonic Anhydrase II", Biochemistry, Nov. 2008, vol. 47(46), pp. 12028-12036.
Maupin, C. et al., "Origins of Enhanced Proton Transport in the Y7F Mutant of Human Carbonic Anhydrase II", J Am Chem Soc., Aug. 2008, vol. 130(34), pp. 11399-11408.
Fisher, S.Z. et al., "Atomic Crystal and Molecular Dynamics Simulation Structures of Human Carbonic Anhydrase II: Insights into the Proton Transfer Mechanism"., Biochemistry, 2007, vol. 46, pp. 2930-2937.

\* cited by examiner

FIG. 2  Native human carbonic anhydrase II    (SEQ ID NO. 1)

```
MSHHWGYGKH  10
NGPEHWHKDF  20
PIAKGERQSP  30
VDIDTHTAKY  40
DPSLKPLSVS  50
YDQATSLRIL  60
NNGHAFNVEF  70
DDSQDKAVLK  80
GGPLDGTYRL  90
IQFHFHWGSL 100
DGQGSEHTVD 110
KKKYAAELHL 120
VHWNTKYGDF 130
GKAVQQPDGL 140
AVLGIFLKVG 150
SAKPGLQKVV 160
DVLDSIKTKG 170
KSADFTNFDP 180
RGLLPESLDY 190
WTYPGSLTTP 200
PLLECVTWIV 210
LKEPISVSSE 220
QVLKFRKLNF 230
NGEGEPEELM 240
VDNWRPAQPL 250
KNRQIKASFK 260
```

Alternate nomenclature of sequence:
MET SER HIS HIS TRP GLY TYR GLY LYS HIS ASN GLY PRO
GLU HIS TRP HIS LYS ASP PHE PRO ILE ALA LYS GLY GLU
ARG GLN SER PRO VAL ASP ILE ASP THR HIS THR ALA LYS
TYR ASP PRO SER LEU LYS PRO LEU SER VAL SER TYR ASP
GLN ALA THR SER LEU ARG ILE LEU ASN ASN GLY HIS ALA
PHE ASN VAL GLU PHE ASP ASP SER GLN ASP LYS ALA VAL
LEU LYS GLY GLY PRO LEU ASP GLY THR TYR ARG LEU ILE
GLN PHE HIS PHE HIS TRP GLY SER LEU ASP GLY GLN GLY
SER GLU HIS THR VAL ASP LYS LYS LYS TYR ALA ALA GLU
LEU HIS LEU VAL HIS TRP ASN THR LYS TYR GLY ASP PHE
GLY LYS ALA VAL GLN GLN PRO ASP GLY LEU ALA VAL LEU
GLY ILE PHE LEU LYS VAL GLY SER ALA LYS PRO GLY LEU
GLN LYS VAL VAL ASP VAL LEU ASP SER ILE LYS THR LYS
GLY LYS SER ALA ASP PHE THR ASN PHE ASP PRO ARG GLY
LEU LEU PRO GLU SER LEU ASP TYR TRP THR TYR PRO GLY
SER LEU THR THR PRO PRO LEU LEU GLU CYS VAL THR TRP
ILE VAL LEU LYS GLU PRO ILE SER VAL SER SER GLU GLN
VAL LEU LYS PHE ARG LYS LEU ASN PHE ASN GLY GLU GLY
GLU PRO GLU GLU LEU MET VAL ASP ASN TRP ARG PRO ALA
GLN PRO LEU LYS ASN ARG GLN ILE LYS ALA SER PHE LYS

SEQUENCE LISTING

```
<160> NUMBER OF SEQ ID NOS: 1

<210> SEQ ID NO 1
<211> LENGTH: 260
<212> TYPE: PRT
<213> ORGANISM: Homo sapiens

<400> SEQUENCE: 1

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260
```

MODIFIED CARBONIC ANHYDRASE ENZYMES AND THEIR USE IN CARBON DIOXIDE SEQUESTRATION AND ELIMINATION

CROSS-REFERENCE TO RELATED APPLICATIONS

This application is related to U.S. Provisional Application No. 61/357,626; filed Jun. 23, 2010 to which priority is claimed under 35 USC §119. This application is incorporated herein in its entirety.

STATEMENT REGARDING FEDERALLY SPONSORED REASEARCH

The present disclosed subject matter was made with U.S. Government support under grant number R01GM25154 awarded by the National Institutes of Health. The U.S. govermant has certain right in the invention.

BACKGROUND OF THE INVENTION

Carbonic anhydrase (EC 4.2.1.1) is a globular zinc metalloenzyme of molecular mass 30,000. The enzyme was discovered in 1933 and has been the subject of intense scientific investigation. Multiple isoforms have been discovered in plant and animal. The enzyme also exists in plant tissues where it is believed to facilitate the transport of carbon dioxide. Red blood cells contain isoenzymes I and II, which are among the most active. Carbonic anhydrase II has among the highest molecular turnover number of known enzymes. One molecule of carbonic anhydrase II can hydrate a million molecules of carbon dioxide in one second. Physiologically, carbonic anhydrase facilitates the removal of carbon dioxide from the mammalian body, among other functions. The general enzyme reaction is shown below in equation 1.

$$CO_2 + H_2O \Longleftrightarrow HCO_3^- + H^+ \quad \text{Equation 1}$$

Carbonic anhydrase has been used in many studies directed at improving or testing of various methods of protein immobilization. The high turnover rate of the enzyme renders it an ideal protein for these types of experiments The presence of carbonic anhydrase in solution facilitates the transfer of carbon dioxide from the gas to the liquid phase and from the liquid phase to the gas phase. This effect is based on the well established laws governing the mass transfer of gases. The management of carbon dioxide has begun to attract the attention of the scientific community, due to the problem of global warming, to the need for fresh water via desalination of ocean and sea water, and to the use of artificial lung machines.

Carbon dioxide emissions have been identified as a major contributor to the phenomenon of global warming. Carbon dioxide is a by-product of combustion and it creates operational, economic, and environmental problems. It is a reaction product without any fuel value, and is an environmental concern since it is the principal greenhouse gas. In addition, because it is an acid gas, carbon dioxide forms carbonic acid in the presence of water, which is corrosive in nature. The removal of this greenhouse gas from the exhaust stream of fossil-fueled industrial processes is a major ecological and economic issue. Moreover, there are few current practical processes for removing carbon dioxide from gaseous streams. As one example, a current process for the removal of carbon dioxide from gaseous emissions purifies the carbon dioxide to a high concentration (e.g., 70 100%), compresses it, and injects it into oil wells as a compressed gas. However, the compressed and highly concentrated toxic carbon dioxide has the potential to escape back into the air. Thus, no method or device for removing carbon dioxide from the exhaust stream of fossil-fueled power plants exists which satisfies the needs of safety, efficiency, and economy. There is often a need to remove carbon dioxide species, including bicarbonate and carbonate and carbonic acid, from solution. For example, in an artificial lung, the vital process is the removal of these carbon dioxide species (defined as carbon dioxide, bicarbonate, carbonate, and carbonic acid) from blood. In the desalination of ocean and sea water, the elimination of carbon dioxide species and recycling of the resulting carbon dioxide is important. See the following U.S. Pat. Nos. 7,083,730, B2; 2005/0145568 A1; 7,459,088 B2; 2009/0297431 A1; US 2010/0108587.

Previous interest in carbon dioxide has been centered around the use of the gas in a variety of the processes. Prior art processes for the management of carbon dioxide are described in the following U.S. Pat. Nos. 3,659,400; 3,853,712; 4,032,616; 4,047,894; 4,162,298; 4,452,676; 4,521,387; 4,710,362; 5,061,455; 5,112,740; 5,609,838; 5,618,506; 5,624,812; 5,565,319; 5,674,463; and 5,690,099.

Also known in prior art, there is the process disclosed in WO 96/40414 in the name of Trachtenberg. Trachtenberg discloses a process for gas separation wherein a selected gas in a mixed gas strew is contacted by an enzyme having an active site directly contacted by the mixed gas stream, and the selected gas is at least partially removed from the mixed gas stream.

EP511719 discloses a process where carbon dioxide is being removed from a gas stream using a enzyme reactor in which carbonic anhydrase is immobilized on a porous substrate.

Moreover, the United States Air Force carried out two investigations in 1965 and 1966 and the possible use of carbonic anhydrase to remove carbon dioxide from space vehicles. The first study explored the absorption of carbon dioxide from an air stream using a closed air loop apparatus. A variety of chemicals alone and/or in combination with CA were evaluated, with respect to their capacity to remove carbon dioxide. The principle conclusion drawn was that the closed air loop system provided an adequate method to study the removal of carbon dioxide from a stream of air. The second study was directed at determining the efficiency of carbon dioxide removal from an air stream using carbonic anhydrase in the presence of various amines. The conclusion reached was that the amine solutions could possibly be used for carbon dioxide absorption and desorption in atmosphere control concepts.

Although many studies relating to the management of carbon dioxide have been conducted in prior art, there is still presently a need for a process and an apparatus that will efficaciously manage carbon dioxide rapidly and at a relatively low cost either for producing carbon dioxide or removing it from a $CO_2$-containing gas.

SUMMARY OF THE INVENTION

The inventors have discovered that by altering the amino acid composition at the catalytic region of the carbonic anhydrase protein (FIG. 2), efficiency and enzymatic activity is dramatically increased. The catalytic region includes those amino acids on the surface of the active-site cavity and the additional amino acids that are in contact with those on the surface of that cavity; this includes, but is not limited to, for example, Thr199, Glu106, His64, Val121, Ile198, Asn62, Asn67, Tyr 7 Trp 209, Val143, Val207 and others. The amino acids at these positions can be altered to produce mutants having modulated activity. These carbonic anhydrase mutant(s) (also referred to as 'modified carbonic anhydrase' or 'MCA') with enhanced activity can be used in a process for the extraction, production of carbon dioxide species defined as carbon dioxide, bicarbonate, carbonate, and carbonic acid and purification of carbon dioxide gas. In a specific embodiment, immobilized MCA contained within a reactor device catalyses the reversible hydration of carbon dioxide The enzyme referred to as MCA includes any of the carbonic anhydrase enzymes from the classes identified as alpha, beta, gamma, and delta. This includes the carbonic anhydrases of plant, animal, and archaeal origins as well as from microorganisms such as cyanobacteria and algae.

According to one embodiment of the present invention, there is provided a method for selectively removing carbon dioxide from a gaseous stream or an aqueous stream. In the first step, gaseous carbon dioxide, such as from factory exhaust, is diffused into a stream of water by flowing the gaseous carbon dioxide through a microporous gas diffusion membrane. It is preferable that the gas diffusion membrane has a high surface area to facilitate a large flow of the gaseous carbon dioxide through the membrane. Removing carbon dioxide from an aqueous stream can omit that step. Next, the carbon dioxide-rich fluid that emerges from the gas diffusion membrane is passed by a matrix that contains a catalyst specific for carbon dioxide. In a preferred embodiment, MCA is used as the catalyst, and bicarbonate is formed. Once bicarbonate is formed, it forms an equilibrium with bicarbonate and carbonate ions, which is pH dependent. Base can then be added to shift the equilibrium to favor the formation of carbonate ions. In the final step, mineral ions such as calcium cations, or magnesium cations are added to the reaction so that a precipitate of carbonate salt is formed. This solid mineral precipitate is at the ground state of energy level of carbon and therefore has the ability to be safely stored for extended periods of time, such as by burying the precipitate in the ground or depositing the precipitate into storage sites either on land or into a body of water. Alternatively, the bicarbonate formed from carbon dioxide can be added to a carbonate slurry, forming bicarbonate, which is then deposited in the ocean with little environmental impact on the surroundings.

According to another embodiment of the present invention, there is provided an apparatus for selectively removing carbon dioxide from a gaseous stream. The apparatus includes a carbon dioxide diffusion module having a gas diffusion membrane to diffuse the carbon dioxide into a stream of water. It is preferable that the gas diffusion membrane has a high surface area to facilitate a large flow of carbon dioxide-saturated air across the membrane. A porous matrix that includes a catalyst, such as MCA, is located in a conversion module. When MCA is used as the catalyst, the speed at which the carbon dioxide is converted to bicarbonate greatly increases. The catalyst can be coupled to the matrix by adsorptive, ionic, or covalent bonding techniques. In addition, the catalyst can be cross-linked or co-cross linked to other chemicals to enhance its activity. Further, the apparatus includes a mineralization module in which a mineral ion is added to a carbonate solution to form a precipitate of carbonate salt. Typically, cations such as, but not limited to, calcium cations, or magnesium cations are added to form the precipitate carbonate salt. In a modification of this process, MCA can be used to remove carbon dioxide species from solution in an artificial lung machine or in desalination. In the lung machine, blood is in contact directly or indirectly with immobilized MCA which enhances conversion of carbon dioxide species into carbon dioxide which is removed from the blood by several possible procedures. In desalination, bicarbonate salts including but not limited to ammonium bicarbonate are osmotic agents drawing water from sea or ocean water. Purification proceeds by removal of the ammonium bicarbonate. In this process, MCA is used to enhance the conversion of carbon dioxide species (mainly bicarbonate) into carbon dioxide, which can be recycled for further use as osmotic agent.

BRIEF DESCRIPTION OF THE DRAWINGS

The advantages of this invention will be apparent upon consideration of the following detailed disclosure of the invention, especially when taken in conjunction with the accompanying drawings wherein:

FIG. 2 shows the amino acid sequence of the human carbonic anhydrase enzyme

DETAILED DESCRIPTION

Figure 1:
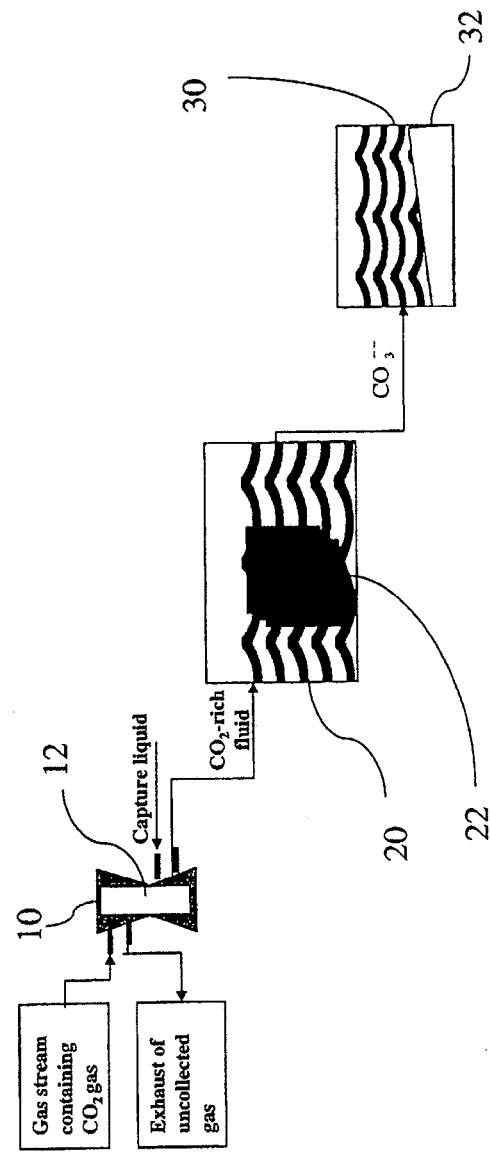
FIG. 1 is a schematic illustration of a process for the removal of $CO_2$ according to the present invention.

The subject invention is based on the inventors discovery that the alteration of the human carbonic anhydrase II to form specific mutants can increase efficiency of the enzyme. Embodiments of such mutants have been noted supra as MCAs. In one embodiment, the invention pertains to a method that involves two steps in the enzyme catalytic steps 1) the conversion of CO2 to bicarbonate and 2) the proton transfer (PT) step—that regenerates the active site Zn—OH ready for the next CO2 molecule.

For step 1) to increase the kcat/Km (overall rate of the reaction) these would include, but are not limited to, combinations of changes to amino acids at positions, typically, for example, Val121, Ile198, Trp209, Val143, Val207 to other amino acids based on the polypeptide sequence shown in FIG. 2. In another embodiment, amino acid positions Thr208 and/or Trp209 are substituted with other amino acids. In a more specific embodiment, the amino acids are substituted with hydrophobic amino acids. Note that the skilled artisan equipped with the teachings of the present disclosure and in view of the known genetic code, and in view of the known nucleic acid sequence that encodes the native human carbonic anhydrase enzyme, can engineer polynucleotide molecules which encode the mutants described herein.

For step 2) to increase the PT rate—If the concentration of $CO_2$ approaches the value of $K_m$ (about 10 mM for wild type CA—and this may well be the fact in an industrial application of the enzyme), then $k_{cat}$ becomes important in overall rate of catalysis and mutants such as Y7F become significant factors in the enzyme reaction.

The inventors have discovered that combining mutant amino acids in combination at positions Tyr7, Asn62, Asn67 to displace solvent molecules in the active site. In a specific example, the inventors have shown a synergetic effect by mutating both positions as follows: Tyr7Phe and Asn67Gln. The Tyr7Phe mutation increases PT by ~7-fold, the double mutant Tyr7Phe/Asn67Gln increases PT by ~10-fold.

The mutants can be achieved according to convention site-specific mutagenesis. The following is a list of references discussing mutagenesis techniques: Ling et al., Approaches to DNA mutagenesis: an overview, Anal Biochem. 254(2): 157-178 (1997); Dale et al., Oligonucleotide-directed random mutagenesis using the phosphorothioate method, Methods Mol. Biol. 57:369-374 (1996); Smith, In vitro mutagenesis, Ann. Rev. Genet. 19:423-462 (1985); Botstein & Shortie, Strategies and applications of in vitro mutagenesis, Science 229:1193-1201 (1985); Carter, Site-directed mutagenesis, Biochem. J. 237:1-7 (1986); Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Bass et al., Mutant Trp repressors with new DNA-binding specificities, Science 242:240-245 (1988); Methods in Enzymol. 100: 468-500 (1983); Methods in Enzymol. 154: 329-350 (1987); Zoller & Smith, Oligonucleotide-directed mutagenesis using M13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8785 (1985); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Sayers et al., 5'-3' Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Improved enzymatic in vitro reactions in the gapped duplex DNA approach to oligonucleotide-directed construction of mutations, Nucl. Acids Res. 16: 7207 (1988); Fritz et al., Oligonucleotide-directed construction of mutations: a gapped duplex DNA procedure without enzymatic reactions in vitro, Nucl. Acids Res. 16: 6987-6999 (1988); Kramer et al., Point Mismatch Repair, Cell 38:879-887 (1984); Carter et al., Improved oligonucleotide site-directed mutagenesis using M13 vectors, Nucl. Acids Res. 13: 4431-4443 (1985); Carter, Improved oligonucleotide-directed mutagenesis using M13 vectors, Methods in Enzymol. 154: 382-403 (1987); Eghtedarzadeh & Henikoff, Use of oligonucleotides to generate large deletions, Nucl. Acids Res. 14: 5115 (1986); Wells et al., Importance of hydrogen-bond formation in stabilizing the transition state of subtilisin, Phil. Trans. R. Soc. Lond. A 317: 415-423 (1986); Nambiar et al., Total synthesis and cloning of a gene coding for the ribonuclease S protein, Science 223: 1299-1301 (1984); Sakmar and Khorana, Total synthesis and expression of a gene for the a-subunit of bovine rod outer segment guanine nucleotide-binding protein (transducin), Nucl. Acids Res. 14: 6361-6372 (1988); Wells et al., Cassette mutagenesis: an efficient method for generation of multiple mutations at defined sites, Gene 34:315-323 (1985); Grundstrom et al., Oligonucleotide-directed mutagenesis by microscale 'shot-gun' gene synthesis, Nucl. Acids Res. 13: 3305-3316 (1985); Mandecki, Oligonucleotide-directed double-strand break repair in plasmids of *Escherichia coli*: a method for site-specific mutagenesis, Proc. Natl. Acad. Sci. USA, 83:7177-7181 (1986); Arnold, Protein engineering for unusual environments, Current Opinion in Biotechnology 4:450-455 (1993); Sieber, et al., Nature Biotechnology, 19:456-460 (2001). W. P. C. Stemmer, Nature 370, 389-91 (1994); and, I. A. Lorimer, I. Pastan, Nucleic Acids Res. 23, 3067-8 (1995). Additional details on many such methods can be found in Methods in Enzymology Volume 154, which also describes useful controls for trouble-shooting problems with various mutagenesis methods.

In view of the teachings herein of modified carbonic anhydrase enzymes, these enzymes can be implemented in systems of sequestering carbon dioxide and/or removing carbon dioxide species from blood or sea water or solution. One example of such a system is taught in U.S. Pat. No. 7,132,090. Applicants provide a summary of the implementation of modified carbonic anhydrase enzymes utilizing the system taught in the '090 patent. Referring to FIG. 1, a schematic illustration of a process according to the present invention can be seen. In the first step, gaseous carbon dioxide, such as from factory exhaust, is diffused into a capturing liquid by flowing the gaseous carbon dioxide through a gas diffusion membrane (12) in a carbon dioxide capture module (10). Hereinafter, the process is described using water as the capturing liquid. Preferably, the gas diffusion membrane (12) has a high surface area to facilitate a large flow of the gaseous carbon dioxide through the membrane (12). Suitable membranes (12) for use in the carbon dioxide capture module (10) include a polypropylene gas exchange membrane, ePTFE (GORE-TEX), zeolites, chytosan, polyvinylpyrollindine, cellulose acetate, and immobilized liquid membranes. Other similar gas diffusion membranes (12) would be easily identified by one of skill in the art. U.S. Pat. No. 6,524,843 teaches another process for sequestering carbon dioxide that may implement modified carbonic anhydrase enzymes.

In the next step, the transformation of dissolved forms of carbon dioxide to bicarbonate are accelerated in a conversion module (20). In particular, the carbon dioxide rich fluid that emerges from the gas diffusion membrane (12) is passed by a matrix (22) that contains a catalyst specific for carbon dioxide, such as modified carbonic anhydrase. Examples of suitable matrixes include beads, fabrics, fibers, membranes, particulates, porous surfaces, rods, and tubes. Specific examples of suitable matrixes include alumina, bentonite, biopolymers, calcium carbonate, calcium phosphate gel, carbon, cellulose, ceramic supports, clay, collagen, glass, hydroxyapatite, ion-exchange resins, kaolin, nylon, phenolic polymers, polyaminostyrene, polyacrylamide, polypropylene, polymerhydrogels, sephadex, sepharose, silica gel, and TEFLON-brand PTFE.

The catalyst may be coupled to the matrix (22) using adsorptive, ionic or covalent binding techniques. The catalyst can be used in its native faun or it can be cross-linked or co-cross linked with other chemicals to enhance its activity. Alternatively, the catalyst can be entrapped in a gel or polymer matrix, stabilized in a micellar structure, incorporated into the substance of the matrix itself, or configured as a membrane reactor, e.g., by using a membrane-enclosed enzyme catalysis (MEEC) technique.

Once the bicarbonate is formed, it spontaneously forms an equilibrium with carbonate ions, which is pH dependent. Base can then be added to shift the equilibrium to favor the formation of carbonate ions. Another alternative is to remove carbon dioxide by bubbling or gaseous diffusion. In the final step, a mineral ion is added to a solution in a mineralization module (30) so that a precipitate of carbonate salt (32) is formed. Typically, calcium cations or magnesium cations are added to precipitate the carbonate salt. This solid mineral precipitate (32) has the ability to be safely stored for extended periods of time, such as by burying the precipitate (32) in the ground or depositing the precipitate (32) into storage sites either on land or into a body of water. Alternatively, the bicarbonate formed from carbon dioxide can be added to a carbonate slurry to form bicarbonate ions, which can then be deposited in the ocean with little environmental impact on the surroundings. In addition, naturally occurring brine and salt aquifers, which are rich sources of counter-ions (e.g. Ca++ and Mg++), can be used as deposition sites for the bicarbonate and/or carbonate formed in the reaction.

The process set forth and generally described in FIG. 1 can be varied in many ways and the catalyst can be used differently depending on the configuration of the process. For example, the diffusion membrane may be altered so that the catalyst is bound directly to the gas exchange membrane. In addition, the catalyst can be cross-linked or co-cross linked with other chemicals to prolong its activity. Alternatively, the catalyst can be affixed to the membrane in a gel or polymer matrix or by being stabilized in a micellar structure. It can be incorporated into the substance of the membrane itself, or configured as a membrane reactor, e.g., by using membrane-enclosed enzyme catalysis (MEEC). By binding the catalyst to the gas diffusion membrane, the efficiency of carbon dioxide capture is increased compared to the membrane alone. For example, the catalyst enhances the specificity of the transfer of carbon dioxide. Because the catalyst reacts specifically with carbon dioxide, it favors the movement of carbon dioxide into the fluid by accelerating the reaction of the dissolved carbon dioxide and water to form bicarbonate, thereby removing carbon dioxide rapidly and allowing the dissolution of carbon dioxide from the gas from the feed stream into the water to a greater extent than it would otherwise. Because of these actions, the efficiency of the membrane-catalyst combination is greater than that of the membrane alone.

The processes for removal of carbon dioxide species is similar to the above. The catalyst enhances the transfer of these species into carbon dioxide. As a gas, carbon dioxide is removed from solution, or from blood, or from the reverse osmosis solution containing ammonium chloride. The same technology applies to these other applications.

The catalyst increases the effectiveness of the gas diffusion membranes by enhancing the specificity of the reaction for carbon dioxide. Because the catalyst specifically reacts with carbon dioxide, other gases are left behind in the gas stream. In addition, the catalyst accelerates the reaction of the dissolved carbon dioxide and water to form bicarbonate, thereby removing carbon dioxide, rapidly influencing mass flux, and causing the reaction to occur to a greater extent than it would otherwise.

In a further alternate embodiment the carbon dioxide capture module and the conversion module are not employed. Instead, the modified carbonic anhydrase may be freely dissolved into a wet scrubbing system. In this alternative embodiment, the gas stream containing the carbon dioxide is bubbled through a solution in which the modified carbonic anhydrase is freely dissolved. The carbon dioxide dissolves into the water and then reacts with the catalyst (e.g., modified carbonic anhydrase) to rapidly form bicarbonate. The solution is then allowed to react as described above to form bicarbonate and carbonate ions, which are then precipitated using appropriate counter ions (e.g. Ca++, Mg++). In a further alternative embodiment the wet scrubbing system is used with the modified carbonic anhydrase attached to a matrix.

The processes described above for capturing carbon dioxide can also be used in hydrogen production, such as in hydrocarbon reforming. The production of hydrogen using the reforming process typically produces large amounts of carbon dioxide. For example, during the process of using hydrocarbon reforming to produce hydrogen, a hydrocarbon feedstock is heated with steam at a high temperature to convert the hydrocarbon to CO and hydrogen. The CO then reacts with the steam to form carbon dioxide and additional hydrogen molecules. The inventive process may then be employed by passing the carbon dioxide and hydrogen through the carbon dioxide capture module, where the carbon dioxide is placed into solution by the action of the membrane. In addition, the hydrogen will diffuse into the water (albeit to a lesser extent than the carbon dioxide) across the membrane. Preferably, experimental parameters are such that the carbon dioxide is rapidly diffused into the water so that the hydrogen has less time to diffuse into the water. One way to achieve this condition is to attach a modified carbonic anhydrase catalyst to the gas diffusion membrane and accelerate the reaction of dissolved carbon dioxide into bicarbonate. If the flow of gas across the membrane is very rapid, this reaction occurs quickly and the carbon dioxide is captured in the water medium before the hydrogen can cross the membrane and go into solution. This enhances the efficiency of the process of separating the carbon dioxide from the hydrogen. It also increases the yield of hydrogen recovered by preventing it from being lost to the water in the carbon dioxide capturing system and increases the amount of hydrogen that remains in the air stream.

RELATED REFERENCES

Maupin C. M., M. G. Saunders, I. F. Thorpe, R. McKenna, D. N. Silverman, G. A. Voth. 2008. Origins of enhanced proton transport in the Y7F mutant of human carbonic anhydrase II. J. Am. Chem. Soc. 130:11399-11408.

Zheng J., B, Sankara Avvaru, C. K. Tu, R. McKenna, D. N. Silverman. 2008. Role of hydrophilic residues in proton transfer during catalysis by human carbonic anhydrase II. Biochemistry 47:12028-12036.

Fisher, S. Z., C. K. Tu, D. Bhatt, L. Govindasamy, M. Agbandje-McKenna, R. McKenna, D. N. Silverman. 2007. Speeding up proton transfer in a fast enzyme: Kinetic and crystallographic studies on the effect of hydrophobic amino acid substitutions in the active site of human carbonic anhydrase II. Biochemistry, 46: 3803-3813.

Fisher, S. Z., C. M. Maupin, M. Budayova-Spano, L. Govindasamy, C. K. To, M. Agbandje-McKenna, D. N. Silverman, G. A. Voth, R. McKenna. 2007. Atomic crystal and molecular dynamics simulation structures of human carbonic anhydrase 11; Insights into the proton transfer mechanism. Biochemistry. 42:2930-2937.

In reviewing the detailed disclosure which follows, and the specification more generally, it should be borne in mind that all patents, patent applications, patent publications, technical publications, scientific publications, and other references referenced herein are hereby incorporated by reference to the extent not inconsistent with the teachings herein.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. An isolated modified carbonic anhydrase (MCA) polypeptide of SEQ ID NO:1, but with a different amino acid substituted in place of position L203 or T208, or both; and optionally a different amino acid substituted in place of position N62, A65, or N67, or combinations thereof.

2. The polypeptide of claim 1 wherein said different amino acid is a hydrophobic amino acid.

3. The polypeptide of claim 1, further comprising a different amino acid substituted in place of position Y7.

4. The polypeptide of claim 3, wherein Y7 is substituted with F.

5. The polypeptide of claim 1, wherein the polypeptide comrisied N67 that is substituted with Q.

6. The polypeptide of claim 1, wherein the polypeptide comprises a different amino acid substituted in place of position L203 and T208.

7. A process for removing an amount of carbon dioxide, bicarbonate, or carbonate from solution, said process comprising: contacting the solution with a catalyst specific for carbon dioxide to accelerate a conversion of the solubilized carbon dioxide, bicarbonate or, carbonate to carbon dioxide, wherein said catalyst is MCA polypeptide of claim 1.

8. The process according to claim 7, further comprising: adding a base forming bicarbonate ions from the carbon dioxide.

9. The process according to claim 8, further comprising: adding a base to form carbonate ions.

10. The process according to claim 7, wherein the mineral ion is selected from the group consisting of sodium cations, calcium cations and magnesium cations.

11. The process according to claim 10, wherein the precipitate is selected from the group consisting of a carbonate salt and a bicarbonate salt.

12. A process for removing carbon dioxide from a gaseous stream comprising: placing the carbon dioxide into solution by passing the gaseous stream through a gas diffusion membrane that contains a catalyst, the catalyst accelerating the conversion of the carbon dioxide to bicarbonate; and adding a mineral ion to form a precipitate of a salt of the bicarbonate, and wherein the catalyst is MCA polypeptide of claim 1.

13. The process of claim 12, further comprising: adding base and forming bicarbonate ions.

14. The process of claim 13, further comprising: adding a base to form carbonate ions.

15. The process according to claim 12, wherein the mineral ion is selected from the group consisting of sodium cations, calcium cations and magnesium cations.

16. The process according to claim 12, wherein the precipitate is selected from the group consisting of a carbonate and a bicarbonate salt.

* * * * *